(12) United States Patent
Acuña et al.

(10) Patent No.: US 6,610,346 B1
(45) Date of Patent: Aug. 26, 2003

(54) MERCAPTO-ALKANOL FLAVOR COMPOUNDS

(75) Inventors: Gonzalo Acuña, Dietikon (CH); Markus Gautschi, Zeiningen (CH); Frank Kumli, Niedererlinsbach (CH); Joachim Schmid, Volketswil (CH); Janos Zsindely, Weisslingen (CH)

(73) Assignee: Givaudan Schweiz AG, Dubendorf (CH)

( * ) Notice: Subject to any disclaimer, the term of this patent is extended or adjusted under 35 U.S.C. 154(b) by 0 days.

(21) Appl. No.: 09/579,633

(22) Filed: May 26, 2000

(30) Foreign Application Priority Data

May 28, 1999 (EP) .............................. 99110416

(51) Int. Cl.$^7$ ................................ A23L 1/22
(52) U.S. Cl. ................. 426/535; 426/534; 426/590; 426/650
(58) Field of Search ................ 426/535, 534, 426/650, 590

(56) References Cited

U.S. PATENT DOCUMENTS

| 3,892,878 A | 7/1975 | Wilson et al. ............. 426/534 |
| 3,970,689 A | 7/1976 | Stoffelsma et al. ......... 260/488 |
| 4,053,656 A | 10/1977 | Stoffelsma et al. |
| 6,231,912 B1 * | 5/2001 | Widder et al. ............. 426/535 |

FOREIGN PATENT DOCUMENTS

| DE | 2316456 | 4/1973 |
| EP | 924198 | 6/1999 |
| GB | 1 423 914 | 2/1976 |

OTHER PUBLICATIONS

Olsen et al., *Onion–like off–flavor in beer: isolation and identification of the culprits*, Carlsberg Res. Commun. (1988) 53(1) (Abstract) Stn Caplus XP 002120546.

Tominaga et al., *Identification of New Volatile Thiols in the Aroma of Vitis Vinifera L. Var. Sauvignon Blanc Wines*, Flavour Fragrance J. 1998, 13, 159.

Engel et al., *Identification of New Sulfur–Containing Volatiles in Yellow Passion Fruits (Passiflora edulis f. flavicarpa)*, J. Agric. Food Chem. 1991, 39, 2249.

Bouchilloux et al., *Identification of Volatile and Powerful Odorous Thiols in Bordeaux Red Wine Varieties*, J. Agric. Food Chem. 1998, 46, 3095.

Holscher et al., *Prenyl Alcohol—Source for Odorants in Roasted Coffee*, J. Agric. Food Chem 1998, 46, 3095.

Werkhoff et al., *Vacuum Headspace Method in Aroma Research: Flavor Chemistry of Yellow Passion Fruits*, Flavour Fragrance J. 1998, 13, 159.

\* cited by examiner

*Primary Examiner*—Leslie Wong
(74) *Attorney, Agent, or Firm*—Wood, Herron & Evans, L.L.P.

(57) ABSTRACT

New 3-mercapto-alkanols are disclosed. The compounds, namely 3-mercapto-2-methyl-butan-1-ol and/or 3-mercapto-3-methyl-hexan-1-ol, and the stereoisomers of each, are used to flavor products, such as foods and/or beverages. Methods for the preparation of both diastereoisomers of 3-mercapto-2-methyl-butan-1-ol are also disclosed.

27 Claims, No Drawings

MERCAPTO-ALKANOL FLAVOR COMPOUNDS

This application claims priority to European Patent Application Serial No. 99110416.7 filed May 28, 1999.

FIELD OF THE INVENTION

The present invention relates to new 3-mercapto-alkanols and their stereoisomers, to flavoring compositions and to food or beverage products flavored with at least one of these compounds, and to a method for the preparation of both diastereoisomers of 3-mercapto-2-methyl-butan-1-ol.

BACKGROUND OF THE INVENTION

In the food and beverage industry flavors play a critical role in the appreciation of food and beverage products. Hereafter the term flavor shall also include aroma and/or taste and in the following context all these terms are used interchangeably.

Several mercapto-alkan-1-ol compounds have been identified as flavorants in food products. Thus, 3-mercapto-hexan-1-ol has been identified in the yellow passion fruit (*Passiflora edulis* f. flavicarpa) (K. -H. Engel, R. Tressel, *J. Agric. Food Chem.* 1991, 39, 2249), in Sauvignon blanc wine (T. Tominaga, A. Furrer, R. Henry, D. Dubourdieu, *Flavour Fragrance J.* 1998, 13, 159; P. Werkhoff, M. G üntert, G. Krammer, H. Sommer, J. Kaulen, *J. Agric. Food Chem.* 1998, 46, 1076), and in red Bordeaux wine (P. Bouchilloux, P. Darriet, R. Henry, V. Lavigne-Cruége, D. Dubourdieu, *J. Agric. Food Chem.* 1998, 46, 3095), and is usually described as having passion fruit and grapefruit character. 3-mercapto-3-methyl-butan-1-ol has been found in roasted coffee (W. Holscher, O. G. Vitzthum, H. Steinhart, *J. Agric. Food Chem.* 1992, 40, 655) and in Sauvignon blanc wine (T. Tominaga, A. Furrer, R. Henry, D. Dubourdieu, *Flavour Fragrance J.* 1998, 13, 159). The flavor description by Holscher et al. is sweet, soup-like.

3-mercapto-2-methyl-propan-1-ol has been identified in red Bordeaux wine (P. Bouchilloux, P. Darriet, R. Henry, V. Lavigne-Cruége, D. Dubourdieu, *J. Agric. Food Chem.* 1998, 46, 3095) and has been described as broth, sweat-like.

The German Offenlegungsschrift 2316456 describes γ-mercapto-alcohols and their formate and acetate esters as important odorants and flavorants that are useful for the preparation and modification of a broad range of flavor compositions. These compounds have been described as faint green, onion-like, sulfury and sweaty with a broad range of taste thresholds.

New 3-mercapto-alkan-1-ols for use as flavor ingredients and/or as flavor enhancer are provided.

SUMMARY OF THE INVENTION

The invention is directed to new 3-mercapto-alkanol compounds. One of these compounds is 3-mercapto-2-methyl-butan-1-ol (formula 1)

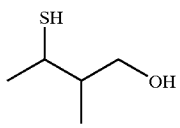

I and stereoisomers of 3-mercapto-2-methyl-butan-1-ol. Another of these compounds is 3-mercapto-3-methyl-hexan-1-ol (formula 11)

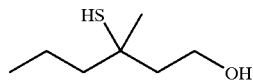

II and stereoisomers of 3-mercapto-3-methyl-hexan-1-ol. In one embodiment, the compound is a stereoisomer of 3-mercapto-2-methyl-butan-1-ol having a relative unlike (u) configuration (formula III)

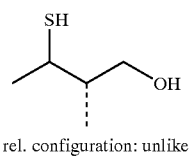

III rel. configuration: unlike or the enantiomer of ll. In an alternative embodiment the compound is a diastereomer of 3-mercapto-2-methyl-butan-1-ol having a relative like (l) configuration (formula IV)

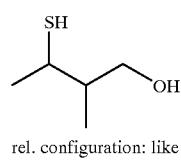

IV rel. configuration: like or the enantiomer of IV.

The above compounds may be used as flavorants in foods and/or beverages. The 3-mercapto-2-methyl-butan-1-ol and stereoisomer compounds provide cooked vegetable and meaty flavor/aroma notes to food products. The (S) isomer of 3-mercapto-3-methyl-hexan-1-ol enhances meaty notes, while the (R) isomer of 3-mercapto-3-methyl-hexan-1-ol enhances natural fruity character of exotic fruit flavors.

The invention is also directed to a flavor composition containing one or a combination of these compounds. In alternative embodiments, the flavor composition contains (rac)-3-mercapto-3-methyl-hexan-1-ol, (S)-3-mercapto-3-methyl-hexan-1-ol, or (R)-3-mercapto-3-methyl-hexan-1-ol. The compound in the flavor composition is at a concentration in the range of about 0.01 ppb to 50 ppm. The invention is also directed to a food or beverage product containing the above flavor compositions.

The invention is further directed to a method of flavoring a product, such as a food, beverage, oral hygiene product, pharmaceutical, or chewing gum, by adding one or a combination of the above compounds in an amount sufficient to flavor the product. The concentration of the compound may be in the range of about 0.01 ppb to 50 ppm.

The invention is still further directed to methods to synthesize 3-mercapto-2-methyl-butan-1-ol and stereoisomers, and 3-mercapto-3-methyl-hexan-1-ol and stereoisomers.

DETAILED DESCRIPTION

It has now been found that two new mercapto-alkanols, namely 3-mercapto-2-methyl-butan-1-ol of formula I

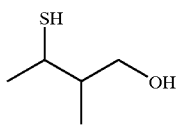

and 3-mercapto-3-methyl-hexan-1-ol of formula II

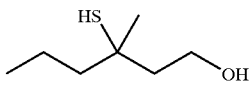

including all possible stereoisomers have very interesting flavor properties that are strongly dependent on the absolute and relative configurations of the compounds.

Especially interesting are the flavor properties of the two diastereoisomeric forms of 3-mercapto-2-methyl-butan-1-ol, namely (u)-3-mercapto-2-methyl-butan-1-ol of formula III

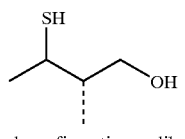

rel. configuration: unlike and (l)-3-mercapto-2-methyl-butan-1-ol of formula IV.

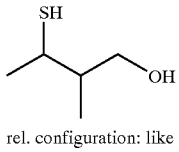

rel. configuration: like

It has been found that the (u)-3-mercapto-2-methyl-butan-1-ol enantiomers of formula III exhibit a strong onion-like note, with a surprisingly extreme low odor threshold value of 4 pg/l air. Due to this extremely strong aroma (u)-3-mercapto-2-methyl-butan-1-ol of formula III is a valuable flavor ingredient, and even at concentrations of down to 0.01 ppb in water, the flavor of these compounds can be recognized. It has been found that the enantiomers of formula III are useful to enhance the meaty, boiled meat character of a food product, especially meat products, at concentrations of 0.1 ppb to 1 ppb and to impart cooked vegetable and meaty notes to food products, especially soup products, at concentrations from 1 ppb to 100 ppb.

It has been further found that the (l)-3-mercapto-2-methyl-butan-1-ol enantiomers of formula IV exhibit a herbaceous, onion-like, leeky and gassy character with a far higher threshold value of about 400 pg/l air as compared to the enantiomers of formula II. Surprisingly, it has been found that this compound is useful to enhance the typical natural, fruity character of exotic fruits at concentrations of 10 ppb to 50 ppm in a food product, preferably at concentrations in the range of 100 ppb to 5 ppm.

The compounds of formulas III and IV are not limited to any particular isomer; all possible enantiomers and all mixtures are thus included within the scope of the invention.

It has also been found that the two enantiomers of 3-mercapto-3-methyl-hexan-1-ol have quite different olfactory properties, the (S)-isomer exhibits herbaceous, agrestic and green notes whereas the (R)-isomer can be described as grapefruit/passion fruit, black currant and onion-like. Both enantiomers exhibit an extremely strong aroma, even at concentrations of down to 0.1 ppb in water, and are therefore valuable flavor ingredients. The (S)-3-mercapto-3-methyl-hexan-1-ol is useful to enhance the flavor properties of food products, especially the meaty, boiled meat character of meat products the cooked vegetable and meaty notes of soup products. The amount of flavorant needed to impart these flavor characteristics depends on the food product to be flavored and is known to the person skilled in the art. Usually the concentrations range from 0.1 ppb to 1 ppm, preferably from 1 ppb to 100 ppb. The (R)-3-mercapto-3-methyl-hexan-1-ol is useful to enhance the typical natural, fruity character of exotic fruit flavors at concentrations of 10 ppb to 50 ppm in a food product, preferably at concentrations in the range of 100 ppb to 5 ppm.

Depending on the desired flavor properties of the finished food or beverage product, 3-mercapto-3-methyl-hexan-1-ol can be used in enantiomerically pure forms or as mixtures thereof.

The 3-mercapto-alkanols of the present invention are useful for flavoring various products such as foods, beverages, chewing gums; oral hygiene products, and pharmaceuticals, but are especially favored for flavoring foods and beverages. The 3-mercapto-alkan-1-ols according to the present invention can be added directly to the product or as flavor compositions comprising usual additives that are well known to a person of skill in the art. The 3-mercapto-alkan-1-ols according to the present invention can also be used in flavoring compositions to enhance or modify existing flavors in order to provide a specific flavor impression. They may then be incorporated into the flavoring compositions exclusively or in combination with further flavor ingredients such as esters, aldehydes, ketones, alcohols, lactones, heterocycles as e.g. furans, pyridines, pyrazines, and other sulfur compounds as e.g. thiols, sulfides, disulfides and the like. As is known to one of skill in the art, these components can be combined in proportions normally used for flavoring preparation.

It may be desirable to prepare the inventive flavoring compositions by using carrier materials, e.g. gum arabic or maltodextrin, or solvents, e.g. ethanol, propyleneglycol, water or triacetin yielding, inter alia, emulsions. By using carrier materials or solvents, the desired physical form of the flavoring composition can be obtained. When the carrier materials form an emulsion, the flavoring composition may further contain emulsifiers such as mono- and diglycerides of fatty acids and the like. The inventive flavoring compositions may be used in spray-dried, liquid, encapsulated, emulsified, or other forms.

The 3-mercapto-alkan-1-ols of the present invention may be used solely or in combination with other flavor ingredients known by those skilled in the art. Thus, a flavor composition may contain one or more of the compounds according to the invention. The total content of one or more of these compounds is preferably in the range of 0.01 ppb to 50 ppm, preferably in the range of 1 ppb to 5 ppm, depending on the product to be flavored.

The invention also provides a procedure for the stereospecific synthesis of the two diastereoisomeric forms of 3-mercapto-2-methyl-butan-1-ol of formula I, namely (u)-3-mercapto-2-methyl-butan-1-ol of formula III and (l)-3-mercapto-2-methyl-butan-1-ol of formula IV.

The procedure for the preparation of (u)-3-mercapto-2-methyl-butan-1-ol comprises the condensation of benzyl mercaptan with angelic acid methyl ester, the reduction of the formed ester with lithium aluminum hydride and subsequent debenzylation with sodium in liquid ammonia. Using this procedure (u)-3-mercapto-2-methyl-butan-1-ol is obtained with a diastereoisomeric purity of >6:1. The isomerically enriched product can be used as such as flavorant to enhance the flavor properties of a food product, or it can be purified by chromatography to get diastereomerically pure (u)-3-mercapto-2-methyl-butan-1-ol, to be

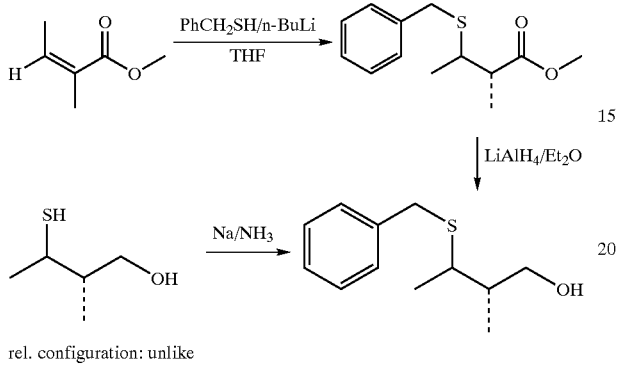

rel. configuration: unlike used as flavorant as described infra.

The procedure for the preparation of (l)-3-mercapto-2-methyl-butan-1-ol comprises the condensation of benzyl mercaptan with tiglic acid methyl ester, the reduction of the formed ester with lithium aluminum hydride and subsequent debenzylation with sodium in liquid ammonia. Using this procedure (l)-3-mercapto-2-methyl-butan-1-ol is obtained with a diastereoisomeric purity of >30:1. The isomerically enriched product can be used as such as flavorant to enhance the flavor properties of a food product, or it can be purified by chromatography to get diastereomerically pure (l)-3-mercapto-2-methyl-butan-1-ol, to be

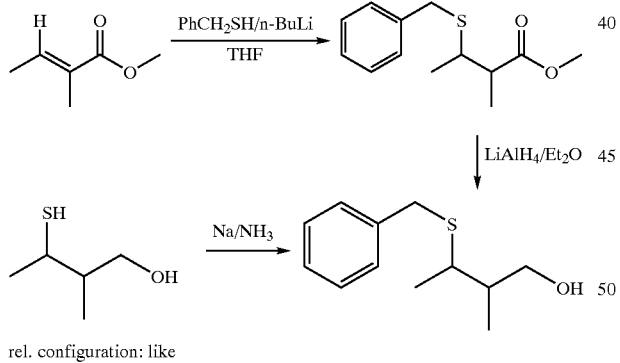

rel. configuration: like used as flavorant as described infra.

The present invention is described further in the following examples showing specific embodiments, which are presented solely for the non-limiting purpose of further illustrating the invention.

EXAMPLE 1

Preparation of (rac)-3-mercapto-3-methyl-hexan-1-ol (a) (rac)-3-Methyl-2-hexenoic acid ethyl ester 35.5 g of NaH (0.8 mol, 60% in oil) was washed two times with hexane and suspended in 450 ml of tetrahydrofuran. The suspension was warmed to 35° C. and under stirring 222.2 g (0.98 mole) of triethyl phosphonoacetate was added such that the internal temperature remained between 35–45° C. Then 100 g (1.16 mol) of 2-pentanone was added over a period of thirty min., maintaining a temperature of 40–45° C., and stirring was continued for 1 h. The reaction mixture was cooled to room temperature and the layers were allowed to separate. The lower layer was taken up in 400 ml of $H_2O$ and was extracted three times with 150 ml of hexane. The upper layer and the hexane layers were combined, dried over $Na_2SO_4$ and concentrated in vacuo and gave 172.4 g of a yellowish oil. Distillation at reduced pressure (42 mbar, 92° C.) yielded 119.4 g (77%) of (rac)-3-methyl-2-hexenoic acid ethyl ester.

| | |
|---|---|
| NMR (CDCl$_3$): | 0.93(t,CH$_3$), 1.27(t,CH$_3$), 1.50(m,CH$_2$,isomer B), 1.51(m,CH$_2$,isomer A, 1.89(d,CH$_3$,isomer B), 2.10(d, CH$_2$,isomer A), 2.16,(d,CH$_3$,isomer A, 2.60(dd,CH$_2$,isomer B), 4.11(q,CH$_2$, isomer B), 4.12(q,CH$_2$,isomer A), 5.67(q,CH) ppm. |
| MS: | 156(26,M$^+$), 128(32), 111(100), 95(38), 82 (49), 69(63), 55(87), 41(66), 29(66). |
| IR (neat): | 2962m, 2936m, 2874w, 1718s, 1649s, 1218s, 1149s, 1106m, 1040m. |

(b) (rac)-3-benzylsulfanyl-3-methyl-hexanoic acid ethyl ester

A mixture of 62.1 g (0.5 mol) of benzyl mercaptan and 78.1 g (0.5 mol) of (rac)-3-methyl-2-hexenoic acid ethyl ester of step (a) in 100 ml of piperidine was heated at reflux until complete reaction was observed (48 h), and cooled to room temperature. Then the excess of piperidine was distilled off at reduced pressure (0.04 mbar, 26–33° C.). The residue, 96.5 g (68%) of (rac)-3-benzylsulfanyl-3-methyl-hexanoic acid ethyl ester, was of good purity and was directly used in the next step.

| | |
|---|---|
| NMR (CDCl$_3$): | 0.90(t,CH$_3$), 1.29(t,CH$_3$), 1.43(s,CH$_3$), 1.40–1.65(m,2CH$_2$), 2.61(s,CH$_2$), 3.75(s, CH$_2$), 4.16(q,CH$_2$), 7.15–7.38(m,5 arom. H) ppm. |
| MS: | 280(3,M$^+$), 235(1), 157(17), 122(27), 91 (100), 83(59), 45(36), 29(51). |
| IR (neat): | 2960m, 2933m, 2872w, 1732s, 1453m, 1198m. |

(c) (rac)-3-benzylsulfanyl-3-methyl-hexan-1-ol

At a temperature of 0° C. to a suspension of 6.8 g (0.18 mol) of LiAlH$_4$ in 200 ml of Et$_2$O was slowly added 50.0 9 (0.18 mol) of (rac)-3-benzylsulfanyl-3-methyl-hexanoic acid ethyl ester of step (b) under stirring such that the temperature did not exceed 10° C. Stirring was continued for 1 h and under cooling acetone and then 400 ml of a saturated NH$_4$Cl solution was slowly added. The reaction mixture was extracted three times with 200 ml of Et$_2$O, the combined organic layers were dried over Na$_2$SO$_4$ and concentrated in vacuo and gave 40.8 g of a yellowish oil. After drying in high vacuo (0.05 mbar/150° C.) 32.5 9 (75%) of (rac)-3-benzylsulfanyl-3-methyl-hexan-1-ol in form of a yellowish oil was obtained.

| NMR (CDCl$_3$): | 0.90(t,CH$_3$), 1.30(s,CH$_3$), 1.35–1.60(m,2 CH$_2$), 1.85(m,CH$_2$), 2.40(br.,OH), 3.73(s, CH$_3$), 3.82(td,CH$_2$), 7.15–7.38(m,5 arom. H) ppm. |
|---|---|
| MS: | 238(4,M$^+$), 114(13), 97(40), 91(89), 55 (100), 41(28). |
| IR (neat): | 3357br, 2957s, 2931s, 2871m, 1453m, 1042m. |

(d) (rac)-3-mercapto-3-methyl-hexan-1-ol

At a temperature of −78° C. to a solution of 16.0 g (67.1 mmol) of (rac)-3-benzylsulfanyl-3-methyl-hexan-1-ol of step (c) in 200 ml of Et$_2$O was added from a cylinder about 200 ml of NH$_3$ Then pieces of Na (ca. 4.0 g) were added until the reaction mixture remained blue for more than 20 min. The blue colored mixture was allowed to warm up to room temperature overnight and EtOH was added until the blue color disappeared. The mixture was then acidified with about 2.7 M of HCl, and extracted three times with 150 ml of Et$_2$O. The combined organic layers were dried over Na$_2$SO$_4$ and concentrated in vacuo. Distillation of the crude product at reduced pressure (40 mbar/130° C.) gave 11.2 g (73%) of (rac)-3-mercapto-3-methyl-hexan-1-ol in form of a colorless oil.

The main flavor was passion fruit, black currant, green.

| NMR (CDCl$_3$): | 0.94(t,CH$_3$), 1.37(s,CH$_3$), 1.38–1.62(m,2 CH$_2$), 1.70(s,SH), 1.88(m,CH$_2$), 2.30(br.,OH), 3.82(td,CH$_2$) ppm. |
|---|---|
| MS: | 148(1,M$^+$), 114(12), 97(25), 71(37), 55 (100), 41(68). |
| IR (neat): | 3346br, 2959s, 2932s, 2872m, 1456m, 1046m. |

EXAMPLE 2

Preparation of (S)-3-mercapto-3-methyl-hexan-1-ol (a) (rac)-3.5-Dinitro-benzoic acid 3-mercapto-3-methyl-hexyl ester To a solution of 5.0 g (34 mmol) of (rac)-3-mercapto-3-methyl-hexan-1-ol in 20 ml of CCl$_4$ was added in portions 8.6 g (37 mmol) of 3,5-dinitrobenzoyl chloride. The mixture was stirred for 72 h, then 10 ml of a saturated NaHCO$_3$ solution was added, the organic layer was separated, washed with 15 ml of brine, dried over MgSO$_4$ and concentrated in vacuo. The residue was purified by flash-chromatography (silicagel, hexane/EtOAc 4:1) and gave 9.8 g (84%) of (rac)-3,5-dinitro-benzoic acid 3-mercapto-3-methyl-hexyl ester.

| NMR (CDCl$_3$): | 0.97(t,CH$_3$), 1.44(s,CH$_3$), 1.40–1.72(m,2 CH$_2$), 1.68(s,SH), 2.12(m,CH$_2$), 4.67(t,CH$_2$), 9.15(d,2H), 9.24(t,1H) ppm. |
|---|---|
| MS: | 342(5,M$^+$), 309(2), 195(9), 103(12), 97(95), 87(25), 55(100), 41(21). |
| IR (neat): | 3101m, 2961m, 2933m, 1732s, 1629m, 1547s, 1463m, 1345s, 1279s, 1168s. |

(b) (1S,3S)-3,5-Dinitro-benzoic acid 3-methyl-3-(4,7,7-trimethyl-3-oxo-2-oxa-bicyclo[2.2.1]heptane-1-carbonylsulfanyl)-hexyl ester To a solution of 9.8 g (28.6 mmol) of (rac)-3,5-dinitro-benzoic acid 3-mercapto-3-methyl-hexyl ester of step (a) and 2.5 g (31.5 mmol) of pyridine in 80 ml of CCl$_4$ was added under stirring 6.82 g (31.5 mmol) of (−)—camphanic acid chloride. The mixture was heated at reflux temperature for 48 h. Another 1.86 g (0.3 eq.) of (−)—camphanic chloride and 0.68 g (0.3 eq.) of pyridine was added and stirring at reflux temperature was continued for 16 h. The mixture was cooled to room temperature, 50 ml of saturated NaHCO$_3$ solution was added and the layers were separated. The organic layer was washed with 40 ml saturated NaHCO$_3$ solution and 40 ml of H$_2$0, dried over MgSO$_4$ and concentrated in vacuo and gave 16.0 g of a yellow oil. Chromatography (silicagel, hexane/EtOAc 4:1) of the crude product yielded 10.0 g of an orange oil. Repeated crystallization from Et$_2$O in the refrigerator gave 1.84 g diastereomerically pure (1 S,3S)-3,5-dinitro-benzoic acid 3-methyl-3-(4,7,7-trimethyl-3-oxo-2-oxa-bicyclo[2.2.1]heptane-1-carbonylsulfanyl)-hexyl ester. X-ray study of crystals grown from CH3CN allowed the determination of the absolute configuration at C-3 to be S.

| NMR (CDCl$_3$): | 0.99(s,CH$_3$), 1.05(s,CH$_3$), 1.10,(s,CH$_3$), 1.21 (t,CH$_3$), 1.35–2.05(m,7H), 1.57(s,CH$_3$), 2.42–2.55(m,3H), 4.58(t,CH$_2$), 9.15(d,2H), 9.23(t,1H) ppm. |
|---|---|
| MS: | 522(0.1,M$^+$), 492(0.5), 309(15), 214(3), 195 (3), 55(62). |
| IR (neat): | 3104m, 2965s, 2934m, 2874m, 1795s, 1734s, 1659s, 1547s, 1463m, 1345s, 1279s, 1166s. |

(c) (S)-3-mercapto-3-methyl-hexan-1-ol

To a suspension of 0.28 g (7.5 mmol) of LiAlH$_4$ in 10 ml of Et$_2$O was added a solution of 1.3 g of (1S,3S)-3,5-dinitro-benzoic acid 3-methyl-3-(4,7,7-trimethyl-3-oxo-2-oxa-bicyclo[2.2.1]heptane-1-carbonylsulfanyl)-hexyl ester of step (b) in 10 ml of THF. The reaction mixture was stirred at room temperature overnight, quenched with 20 ml of water and filtered over Celite. The organic layer was separated, dried over MgSO$_4$ and concentrated in vacuo. The residue was distilled (bulb to bulb, 0.06 Torr, up to 190° C.) and gave 100 mg (27%) of (S)-3-mercapto-3-methyl-hexan-1-ol in form of a colorless oil.

| NMR (CDCl$_3$): | 0.94(t,CH$_3$), 1.37(s,CH$_3$), 1.38–1.62(m,2 CH$_2$), 1.70(s,SH), 1.88(m,CH$_2$), 2.30(br.,OH), 3.82(t,CH$_2$) ppm. |
|---|---|
| [α]$_D^{22}$: | −2.5 (c = 0.8, CHCl$_3$) |

The main flavor was herbaceous, agrestic, green

EXAMPLE 3

Preparation of (l)-3-mercapto-2-methyl-butan-1-ol (racemic) (a) (l)-3-benzylsulfanyl-2-methyl-butyric acid methyl ester At a temperature of 0° C. to a solution of 13.0 ml of n-BuLi (1.6 M in hexane) in 500 ml of THF was added under stirring 236 ml (2.0 mol) of benzyl mercaptan. Then a solution of 23.6 g (0.2 mol) of tiglic acid methyl ester in 500 ml of THF was added. The reaction mixture was allowed to warm up to room temperature and stirring was continued for 3.5 h. The reaction mixture was quenched with 200 ml of a 5% NaOH solution and the organic layer was separated and dried over MgSO$_4$. THF and benzyl mercaptan were distilled off in vacuo (rotary evaporator, 10 mbar/60° C.) and the residue was distilled (0.1 mbar, 110–118° C.) and gave 40.8 g (85.7%) (l)-3-benzylsulfanyl-2-methyl-butyric acid methyl ester in the form of a colorless oil having a diastereoisomeric purity of 98:2 (NMR).

| | |
|---|---|
| NMR (CDCl$_3$): | 1.22(d,CH$_3$), 1.28(d,CH$_3$), 2.57(m,CH), 2.96 (m,CH), 3.64(s,CH$_3$), 3.72(s,CH$_2$), 7.15–7.35 (m,5 arom. H) ppm. |
| MS: | 238(3,M$^+$), 151(3), 147(15), 123(27), 91 (100), 59(18). |
| IR (neat): | 3028w, 2977m, 2950m, 1736s, 1495m, 1453s, 1200m. |

(b) (l)-3-benzylsulfanyl-2-methyl-butan-1-ol

At a temperature of 0° C. to a suspension of 4.78 g (126 mmol) of LiAlH$_4$ in 150 ml of Et$_2$O was added a solution of 20.0 g (84 mmol) of (l)-3-benzylsulfanyl-2-methyl-butyric acid methyl ester of step (a) in 100 ml of Et$_2$O. The reaction mixture was allowed to warm up to room temperature, stirring was continued for 5 h. Then H$_2$0 was slowly added until no more H$_2$ evolution was observed. The reaction mixture was filtered over Celite, the organic layer was dried over MgSO$_4$ and concentrated in vacuo. Distillation of the crude product at reduced pressure (0.05 Torr/110° C.) gave 15.5 g (87%) of (l)-3-benzylsulfanyl-2-methyl-butan-1-ol.

| | |
|---|---|
| NMR (CDCl$_3$): | 0.89(d,CH$_3$), 1.29(d,CH$_3$), 1.60(t,OH), 1.87 (m,CH), 2.84(qd,CH), 3.37–3.68(m,CH$_2$), 3.74(d,CH$_2$), 7.18–7.38(m,5 arom. H) ppm. |
| MS: | 210(6,M$^+$), 151(7), 123(9), 91(100), 45 (17),31(8). |
| IR (neat): | 3381br, 3028w, 2961s, 2921s, 2875s, 1494m, 1452s, 1029s. |

(c) (l)-3-mercapto-2-methyl-butan-1-ol

About 200 ml of NH$_3$ were condensed from a cylinder into a cold flask at −78° C. and small pieces of Na were added until a blue color persisted. Then, under stirring, 3.47 g (64 mmol) of (l)-3-benzylsulfanyl-2-methyl-butan-1-ol were added in small portions. Since the reaction mixture became colorless, the Na addition was continued until a blue color persisted again. Stirring at −78° C. was continued for 1 h, then the mixture was quenched with saturated NH$_4$Cl solution until it became colorless, acidified with 100 ml 2N HCl and extracted with Et$_2$O. The combined organic layers were dried over MgSO$_4$ and concentrated in vacuo. The crude product was distilled at reduced pressure over a 10 cm Vigreux-column (0.15 Torr/60° C.) and gave 5.8 g (86%) (l)-3-mercapto-2-methyl-butan-1-ol in the form of a colorless oil having a diastereoisomeric purity of 40:1 (NMR).

| | |
|---|---|
| NMR (CDCl$_3$): | 0.90(d,CH$_3$), 1.28(d,SH), 1.37(d,CH$_3$), 1.72 (s,OH), 1.86(m,CH), 3.28(m,CH), 3.60(m,CH$_2$)ppm. |
| MS: | 120(12,M$^+$), 102(3), 86(55), 71(60), 61(89), 45(89), 41(100), 31(83). |
| IR (neat): | 3356br, 2964s, 2926s, 2876s, 1450m, 1379m, 1039s. |

The main flavor was herbaceous, onion-like, leeky, gassy.

EXAMPLE 4

Preparation of (u)-3-mercapto-2-methyl-butan-1-ol (racemic) (a) (u)-3-benzylsulfanyl-2-methyl-butyric acid methyl ester At a temperature of 0° C., to a solution of 13.0 ml of n-BuLi (1.6 M in hexane) in 500 ml of THF, was added 236 ml (2.0 mol) of benzyl mercaptan. Then a solution of 23.6 g (0.2 mol) of angelic acid methyl ester in 500 ml of THF was added. The reaction mixture was stirred at 0° C. for 3.5 h, quenched with 200 ml of a 5% NaOH solution. The organic layer was separated and dried over MgSO$_4$. THF and benzyl mercaptan were distilled off in vacuo (rotary evaporator, 10 mbar/60° C.) and the residue was distilled (0.1 mbar, 104–130° C.) and gave 28.2 g (59%) (u)-3-benzylsulfanyl-2-methyl-butyric acid methyl ester in form of a colorless oil having a diastereoisomeric purity of 9:1 (NMR).

| | |
|---|---|
| NMR (CDCl$_3$): | 1.18(d,CH$_3$), 1.20 (d,CH$_3$), 2.65(m,CH), 3.03 (m,CH), 3.66(s,CH$_3$), 3.72(s,CH$_2$), 7.15–7.35 (m,5 arom. H)ppm. |
| MS: | 238(3,M$^+$), 151(2), 147(12), 123(22), 91 (100). |
| IR (neat): | 3029w, 2975m, 1736s, 1495m, 1453s, 1199m. |

(b) (u)-3-benzylsulfanyl-2-methyl-butan-1-ol

At a temperature of 0° C. to a suspension of 4.78 g (126 mmol) of LiAlH$_4$ in 150 ml of Et$_2$O was added under stirring a solution of 20.0 g (84 mmol) of (u)-3-benzylsulfanyl-2-methyl-butyric acid methyl ester in 100 ml of Et$_2$O. The reaction mixture was allowed to warm up to room temperature and stirring was continued for 5 h. Then H$_2$O was slowly added until no more H$_2$ evolution was observed. The reaction mixture was filtered over Celite, the organic layer was dried over MgSO$_4$ and concentrated in-vacuo. Distillation of the crude product at reduced pressure (0.05 Torr/100° C.) gave 14.7 g (83%) of (u)-3-benzylsulfanyl-2-methyl-butan-1-ol having a diastereoisomeric purity of 6.5:1 (NMR).

| | |
|---|---|
| NMR (CDCl$_3$): | 0.95(d,CH$_3$), 1.22(d,CH$_3$), 1.73(t,OH), 1.86 (m,CH), 2.78(m,CH), 3.53(m,CH$_2$), 3.74(d, CH$_2$), 7.18–7.38(m,5 arom. H) ppm. |
| MS: | 210(6,M$^+$), 151(7), 123(9), 91(100), 45(17). |
| IR (neat): | 3377br, 3028w, 2963s, 2923s, 2875s, 1494m, 1452s, 1029s. |

(c) (u)-3-benzylsulfanyl-2-methyl-butan-1-ol

About 200 ml of NH$_3$ were condensed into a flask at −78° C. and small pieces of Na were added until a blue color persisted. Then under stirring 9.5 g (40 mmol) of (u)-3-benzylsulfanyl-2-methyl-butan-1-ol of step (b) were added in small portions. Since the reaction mixture became colorless, Na addition was continued until a blue color persisted again. Stirring at −78° C. was continued for 1 h, the mixture was quenched with saturated NH$_4$Cl solution until it became colorless, acidified with 100 ml 2N HCl and extracted with Et$_2$O. The combined organic layers were dried over MgSO$_4$ and concentrated in vacuo. The crude product was distilled at reduced pressure over a 10 cm Vigreux-column (0.06 Torr/47° C.) and gave 3.0 g (62%) (u)-3-mercapto-2-methyl-butan-1-ol in the form of a colorless oil having a diastereoisomeric purity of 6.5:1.

| | |
|---|---|
| NMR (CDCl$_3$): | 1.00(d,CH$_3$), 1.35(d,CH$_3$), 1.51(d,SH), 1.78 (m,CH), 1.97(br,OH), 3.08(m,CH), 3.65(d, CH$_2$). |
| MS: | 120(13,M$^+$), 102(4), 86(58), 71(62), 61(90), 45(79), 41(100), 31(76). |
| IR (neat): | 3353br, 2965s, 2928s, 2876s, 1449m, 1379m, 1034s. |

The main flavor was strong onion-like, brothy character.

EXAMPLE 5

Flavor tests in food

A meat base having the following composition (parts by weight), was prepared:

| | |
|---|---|
| water | 10 |
| HVP | 30 |
| thiamin HCl | 10 |
| smoke extract | 50 |
| total | 100 |

With this meat base the following bouillons were prepared:
Bouillon A (reference) starting material: bouillon fat free addded thereto:

| | |
|---|---|
| meat base | 100 ppm |

Bouillon B starting material: bouillon fat free added thereto:

| | |
|---|---|
| meat base | 100 ppm |
| (rac)-(u)-3-mercapto-2-methyl-butan-1-ol | 1 ppb |

Bouillon C starting material: bouillon fat free added thereto:

| | |
|---|---|
| meat base | 100 ppm |
| (R)-3-mercapto-3-methyl-hexan-1-ol | 1 ppb |

Bouillons A and B were compared in a blind test by an expert panel of six flavorists. The panel judged bouillon B to have a fuller, more bouillon-like aroma with increased meaty and fatty notes.

Bouillons A and C were compared in a blind test by an expert panel of six flavorists. The panel judged bouillon C to have a fuller, sweeter, more bouillon-like aroma with increased chicken-meat, fatty and onion notes.

Thus, in both tests the present flavor components enhanced the bouillon or meat character, respectively.

EXAMPLE 6

Flavor test in beverage

Flavoring compositions A and B having a passion fruit flavor were prepared using the following ingredients (parts by weight):

| Ingredient | A | B |
|---|---|---|
| Hexyl butyrate | 96 | 96 |
| Ethyl hexanoate | 82 | 82 |
| cis-3-Hexenol | 86 | 86 |
| Linalool | 31 | 31 |
| Hexanal | 9 | 9 |
| Citral | 11 | 11 |
| Methyl 2-octenoate | 34 | 34 |
| Furonol | 48 | 48 |
| Hexanoic acid | 68 | 68 |
| Orange oil | 247 | 207 |
| Ocimene | 69 | 69 |
| 2-Methyl-heptanoic acid | 27 | 27 |
| 2-Hexenoic acid | 137 | 137 |
| cis-3-Hexenyl acetate | 55 | 55 |
| (rac)-3-Mercapto-3-methyl-hexan-1-ol | — | 40 |
| Total | 1000 | 1000 |

The passion fruit flavoring compositions A and B were added, at two drops per 100 ml beverage (about 200 mg/l), to a standard still beverage that was prepared by 1+5 dilution of a beverage syrup of the following composition (parts by weight):

| Ingredient | |
|---|---|
| Sugar Syrup, 65 Bx | 1033 |
| Sodium benzoate | 1 |
| Trisodium citrate | 2 |
| Citric acid anhydrous, 50% w/w in water | 30 |

Water, cold, filled up to 1 000 ml

The thus prepared passion fruit drink AA containing the flavoring composition A, and the passion fruit drink BB containing the flavoring composition B with about 5 ppm of a compound of the present invention, namely (rac)-3-mercapto-3-methyl-hexan-1-ol, were evaluated in a blind test by an expert panel of six flavorists. The panel judged the passion fruit drink BB to have a more rounded off passion fruit flavor with typical exotic fruit character, having a greener, fresher and fruitier character than fruit drink AA.

While the invention has been illustrated and described with respect to illustrative embodiments and modes of practice, it will be apparent to those skilled in the art that various modifications and improvements may be made without departing from the scope and spirit of the invention. Accordingly, the invention is not be limited to the illustrative embodiments and modes or practice.

What is claimed is:

1. A flavor composition comprising a 3-mercapto-alkan-1-ol selected from the group consisting of a (u)-3-mercapto-2-methyl-butan-1-ol (formula III) diastereoisomer of 3-mercapto-2-methyl-butan-1-ol and enantiomers thereof having a meaty cooked vegetable taste and an odor threshold of 4 pg/l air,

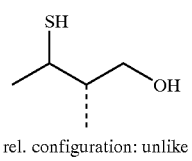

rel. configuration: unlike a (l)-3-mercapto-2-methyl-butan-1-ol (formula IV) a diastereoisomer of 3-mercapto-2-methyl-butan-1-ol and enantiomers thereof having a herbaceous onion-like leeky gassy taste and an odor threshold of 400 pg/l air,

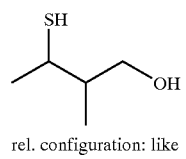

rel. configuration: like and combinations thereof.

2. The composition of claim 1 comprising (S)-3-mercapto2-methyl-butan-1-ol.

3. The composition of claim 1 comprising (R)-3mercapto2-methyl-butan-1-ol.

4. The composition of claim 1, wherein said compound or combinations thereof is at a concentration in the range of about 0.01 ppb to 50 ppm.

5. The composition of claim 4 wherein said concentration is in the range of about 1 ppb to 5 ppm.

6. A food or beverage product containing a flavor/aroma composition comprising a 3-mercapto-alkan-1-ol selected from the group consisting of a (u)-3-mercapto-2-methyl-butan-1-ol (formula III) diastereoisomer of 3-mercapto-2-methyl-butan-1-ol and enantiomers thereof having a meaty cooked vegetable taste and an odor threshold of 4 pg/l air,

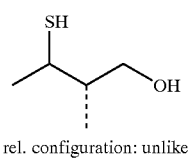

rel. configuration: unlike a (l)-3-mercapto-2-methyl-butan-1-ol (formula IV) diastereoisomer of 3-mercapto-2-methyl-butan-1-ol and enantiomers thereof having a herbaceous onion-like leeky gassy taste and an odor threshold of 400 pg/l air,

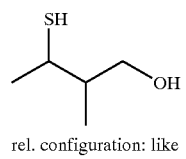

rel. configuration: like and combinations thereof.

7. A method of flavoring a food or beverage product comprising adding a flavor composition comprising a 3-mercapto-alkan-1-ol selected from the group consisting of a (u)-3-mercapto-2-methyl-butan-1-ol (formula III) diastereoisomer of 3-mercapto-2-methyl-butan-1-ol and enantiomers thereof having a meaty cooked vegetable taste and an odor threshold of 4 pg/l air,

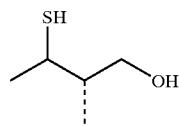

rel. configuration: unlike a (l)-3-mercapto-2-methyl-butan-1-ol (formula IV) diastereoisomer of 3-mercapto-2-methyl-butan-1-ol and enantiomers thereof having a herbaceous onion-like leeky gassy taste and an odor threshold of 400 pg/l air,

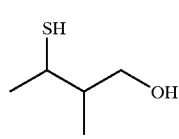

rel. configuration: like and combinations thereof.

8. The method of claim 7 wherein said amount produces a concentration in the range of about 0.01 ppb to 50 ppm.

9. The method of claim 7 wherein said amount is in the range of about 1 ppb to 5 ppm.

10. The method of claim 5 wherein said product is selected from a food product, a beverage product, an oral hygiene product, a pharmaceutical, chewing gum, and combinations thereof.

11. The method of claim 10 wherein said product is selected from the group consisting of a meat product, a vegetable product, and combinations thereof.

12. The method of claim 7 wherein said flavoring is selected from the group consisting of onion-like brothy, herbaceous onion-like leeky gassy, herbaceous agrestic green, grapefruit/passion fruit black currant green, and combinations thereof.

13. The method of claim 7 wherein said composition is added to said food or beverage product in a form consisting of spray dried, liquid, encapsulated, emulsified, and combinations thereof.

14. A flavorant composition comprising (u)-3-mercapto-2-butan-1-ol (formula III)

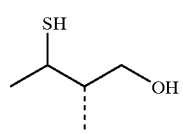

rel. configuration: unlike having a meaty cooked vegetable taste and an odor threshold of 4 pg/l air.

15. A flavorant composition comprising (u)-3-mercapto-2-butan-1-ol (formula III)

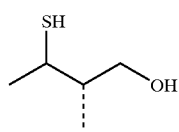

rel. configuration: unlike having a meaty cooked vegetable taste and an odor threshold of 4 pg/l air at a concentration of at least 0.01 ppb in water.

16. A method of flavoring a food or beverage product comprising providing (u)-3-mercapto-2-butan-1-ol (formula III)

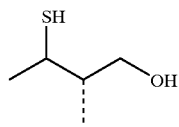

rel. configuration: unlike having a meaty cooked vegetable taste and an odor threshold of 4 pg/l air to the food or beverage product at a concentration of at least 0.1 ppb.

17. A method of flavoring a food or beverage product comprising providing (u)-3-mercapto-2-butan-1-ol (formula III)

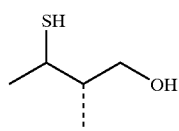

rel. configuration: unlike having a meaty cooked vegetable taste and an odor threshold of 4 pg/l air to the food or beverage product at a concentration in the range of about 0.1 ppb to about 100 ppb.

18. A flavorant composition comprising (l)-3-mercapto-2-butan-1-ol (formula IV)

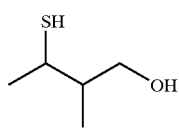

rel. configuration: like having a herbaceous onion-like leeky gassy taste and an odor threshold of 400 pg/l air.

19. A method of flavoring a food or beverage product comprising providing (l)-3-mercapto-2-butan-1-ol (formula IV)

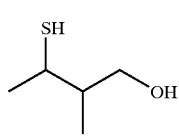

rel. configuration: like having a herbaceous onion-like leeky gassy taste and an odor threshold of 400 pg/l air to the food or beverage product at a concentration of at least 10 ppb.

20. A method of flavoring a food or beverage product comprising providing (l)-3-mercapto-2-butan-1-ol (formula IV)

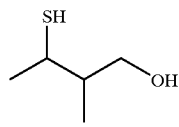

rel. configuration: like having a herbaceous onion-like leeky gassy taste and an odor threshold of 400 pg/l air to the food or beverage product at a concentration in the range of about 10 ppb to about 5 ppm.

21. A food or beverage product containing a flavor/aroma composition comprising (u)-3-mercapto-2-butan-1-ol (formula III)

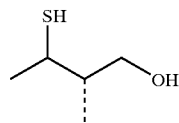

rel. configuration: unlike having a meaty cooked vegetable taste and an odor threshold of 4 pg/l air.

22. A food or beverage product containing a flavor/aroma composition comprising (u)-3-mercapto-2-butan-1-ol (formula III)

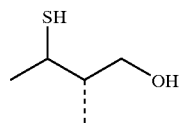

rel. configuration: unlike having a meaty cooked vegetable taste and an odor threshold of 4 pg/l air at a concentration of at least 0.01 ppb in water.

23. A food or beverage product containing a flavor/aroma composition comprising (u)-3-mercapto-2-butan-1-ol (formula III)

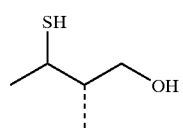

rel. configuration: unlike having a meaty cooked vegetable taste and an odor threshold of 4 pg/l air at a concentration of at least 0.1 ppb.

24. A food or beverage product containing a flavor/aroma composition comprising (u)-3-mercapto-2-butan-1-ol (formula III)

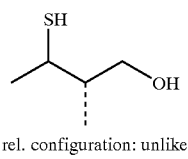

rel. configuration: unlike having a meaty cooked vegetable taste and an odor threshold of 4 pg/l air at a concentration of at least about 0.1 ppb.

25. A food or beverage product containing a flavor/aroma composition comprising (u)-3-mercapto-2-butan-1-ol (formula III)

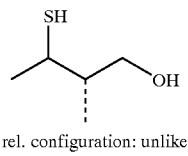

rel. configuration: unlike having a meaty cooked vegetable taste and an odor threshold of 4 pg/l air at a concentration in the range of about 0.1 ppb to about 100 ppb.

26. A food or beverage product containing a flavor/aroma composition comprising (l)-3-mercapto-2-butan-1-ol (formula IV)

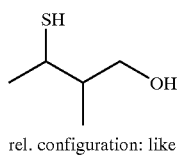

rel. configuration: like having a herbaceous onion-like leeky gassy taste and an odor threshold of 400 pg/l air at a concentration of at least 10 ppb.

27. A food or beverage product containing a flavor/aroma composition comprising (l)-3-mercapto-2-butan-1-ol (formula IV)

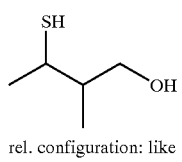

rel. configuration: like having a herbaceous onion-like leeky gassy taste and an odor threshold of 400 pg/l air at a concentration in the range of about 10 ppb to about 5 ppm.

* * * * *

UNITED STATES PATENT AND TRADEMARK OFFICE
CERTIFICATE OF CORRECTION

PATENT NO.    : 6,610,346 B1
DATED         : August 26, 2003
INVENTOR(S)   : Acuna et al.

It is certified that error appears in the above-identified patent and that said Letters Patent is hereby corrected as shown below:

Column 1,
Line 58, "…(formula 1)" should be -- …(formula I) --.

Column 2
Line 3, "…(formula 11)" should be -- …(formula II) --.
Line 23, "… of 11." should be -- … of III --.

Column 3,
Line 9, "…of formula 11" should be -- …of formula II --.
Line 58, "…of forula 11" should be -- …of formula III --.

Column 5,
Lines 20 and 48, the arrow under "Na/NH$_3$" should be pointing as follows: -- ← --.

Column 6,
Line 55, "…50.0 9 (0.18 mol)…" should be -- …50.0g (0.18 mol) --.
Line 65, "…32.5 9 (75%) …" should be -- …32.5 g (75%) --.

Column 13,
Line 25, "…comprising (S)-3-mercapto2-methyl-butan-1-ol." should be -- …comprising (S)-3-mercapto-2-methyl-butan-1-ol. --.
Line 27, "…comprising (R)-3mercapto2-methyl-butan-1-ol." should be -- …comprising (R)-3-mercapto-2-methyl-butan-1-ol. --.

Column 14,
Line 33, "The method of claim 5 wherein…" should be -- The method of claim 7 wherein… --.
Line 65, "…threshold of 4 pg/I air…" should be -- …threshold of 4 pg/1 air… --.

UNITED STATES PATENT AND TRADEMARK OFFICE
CERTIFICATE OF CORRECTION

PATENT NO. : 6,610,346 B1
DATED : August 26, 2003
INVENTOR(S) : Acuna et al.

It is certified that error appears in the above-identified patent and that said Letters Patent is hereby corrected as shown below:

<u>Column 16,</u>
Lines 15 and 48, "...threshold of 4 pg/I air..." should be -- ...threshold of 4 pg/1 air... --.

Signed and Sealed this

Twenty-first Day of March, 2006

JON W. DUDAS
*Director of the United States Patent and Trademark Office*